US009181194B2

(12) United States Patent
Murphy et al.

(10) Patent No.: US 9,181,194 B2
(45) Date of Patent: Nov. 10, 2015

(54) PRODUCTION OF CAPROLACTAM FROM CARBOHYDRATE-CONTAINING MATERIALS

(75) Inventors: Vincent J. Murphy, San Jose, CA (US); Eric L. Dias, Belmont, CA (US); James A. W. Shoemaker, Gilroy, CA (US); Thomas R. Boussie, Menlo Park, CA (US); Zachary M. Fresco, Santa Rosa, CA (US)

(73) Assignee: Rennovia Inc., Santa Clara, CA (US)

( * ) Notice: Subject to any disclaimer, the term of this patent is extended or adjusted under 35 U.S.C. 154(b) by 576 days.

(21) Appl. No.: 13/434,756

(22) Filed: Mar. 29, 2012

(65) Prior Publication Data

US 2012/0264908 A1  Oct. 18, 2012

Related U.S. Application Data

(60) Provisional application No. 61/475,177, filed on Apr. 13, 2011.

(51) Int. Cl.
*C07D 223/10* (2006.01)
*C07C 227/16* (2006.01)
*C07C 231/02* (2006.01)
*C07C 231/12* (2006.01)
*C08G 69/16* (2006.01)

(52) U.S. Cl.
CPC ............ *C07D 223/10* (2013.01); *C07C 227/16* (2013.01); *C07C 231/02* (2013.01); *C07C 231/12* (2013.01); *C08G 69/16* (2013.01)

(58) Field of Classification Search
CPC .. C07C 227/16; C07C 231/02; C07C 231/12; C07D 223/10; C08G 69/16
USPC .......................... 528/323; 562/526, 515, 567
See application file for complete search history.

(56) References Cited

U.S. PATENT DOCUMENTS

| 2,016,962 | A |  | 10/1935 | Flint et al. |
| 2,197,540 | A |  | 4/1940 | Klug |
| 3,211,785 | A | * | 10/1965 | Kilroy et al. .................. 562/526 |
| 4,745,221 | A |  | 5/1988 | Roffia et al. |
| 5,449,770 | A |  | 9/1995 | Shumate et al. |
| 5,625,098 | A |  | 4/1997 | Kao et al. |
| 5,723,673 | A |  | 3/1998 | Kao et al. |
| 6,265,574 | B1 |  | 7/2001 | Kitamura et al. |
| 6,365,778 | B1 |  | 4/2002 | Gallas et al. |
| 6,372,939 | B1 |  | 4/2002 | Bunel et al. |
| 6,429,335 | B1 |  | 8/2002 | Kiel |
| 6,462,235 | B1 |  | 10/2002 | Thiele et al. |
| 6,521,779 | B1 |  | 2/2003 | Boschat et al. |
| 6,894,163 | B2 |  | 5/2005 | Tsunoda et al. |
| 7,439,388 | B2 |  | 10/2008 | Harichian et al. |
| 2007/0299269 | A1 |  | 12/2007 | Harichian |
| 2010/0317823 | A1 | * | 12/2010 | Boussie et al. .................. 528/323 |

FOREIGN PATENT DOCUMENTS

| EP | 0536939 | A1 | 4/1993 |
| JP | 2003-267939 | A | 9/2003 |
| WO | 95/19951 | A1 | 7/1995 |
| WO | 01/96294 | A1 | 12/2001 |
| WO | 2008/006748 | A1 | 1/2008 |
| WO | 2010/041943 | A2 | 4/2010 |
| WO | 2010/041943 | A3 | 7/2010 |
| WO | 2010/144862 | A2 | 12/2010 |
| WO | 2010/144862 | A3 | 3/2011 |

OTHER PUBLICATIONS

Chaveriat et al., "The direct synthesis of 6-amino-6-deoxyaldonic acids as monomers for the preparation of polyhydroxylated nylon 6," Tetrahedron Asymmetry, 17 (2006) 1349-1354.*
Coman et al., "Metal-triflate ionic liquid systems immobilized onto mesoporous MS41 materials as new and efficient catalysts for N-acylation," Journal of Catalysis 249 (2007) 359-369.*
Wuts, P.G.M., and Greene, T.W., "Greene's Protective Groups in Organic Synthesis," 4th Edition, John Wiley and Sons, 2007.*
Korovchenko et al., "Oxidation of primary alcohols with air on carbon-supported platinum catalysts for the synthesis of aldehydes or acids," Catalysis Today 121 (2007) 13-21.*
Raghunathan, et al., "E-Aminocaproic acid and Clinical Value in Cardiac Anesthesia," Journal of Cardiothoracic and Vascular Anesthesia, vol. 25, No. 1 (Feb.), 2011, 16-19.*
Invitation to Pay Additional Fees received for PCT Patent Application No. PCT/US2012/031284, mailed on Jun. 21, 2012, 4 pages.
Pitt et al., "Synthesis of a Glucuronic Acid and Glucose Conjugate Library and Evaluation of Effects on Endothelial Cell Growth", Carbohydrate Research, vol. 339, 2004, pp. 1873-1887.
Marsh et al., "The Synthesis of Aryl Glycosiduronic Acids", Journal Biochem, vol. 68, 1958, pp. 617-621.
Chaveriat et al., "The Direct Synthesis of 6-Amino-6-Deoxyaldonic Acids as Monomer for the Preparation of Polyhydroxylated Nylon 6", Tetrahedron: Asymmetry, vol. 17, 2006, pp. 1349-1354.
International Search Report and Written Opinion received for PCT Patent Application No. PCT/US2012/31284, mailed on Aug. 9, 2012, 18 pages.
Biella et al., "Application of Gold Catalysts to Selective Liquid Phase Oxidation", Catalysis Today, vol. 72, 2002, pp. 43-49.
Dalpathado et al., "Reductive Amination of Carbohydrates using NaBH(OAc)3", Analytical and Bioanalytical Chemistry, vol. 381, 2005, pp. 1130-1137.

(Continued)

*Primary Examiner* — Paul A Zucker
*Assistant Examiner* — Mark Luderer
(74) *Attorney, Agent, or Firm* — Rennovia IP Department

(57) ABSTRACT

The present invention generally relates to processes for the conversion of glucose to caprolactam employing chemocatalytic oxidation and reduction reactions. The present invention also includes processes for the conversion of glucose to caprolactam via amido polyhydroxy acid products and amidocaproic acid or derivatives thereof. The present invention also includes processes that catalytically oxidize an amidopolyol to amidopolyhydroxy acid or derivatives thereof, and processes that catalytically hydrodeoxygenate amino or amido polyhydroxy acid or derivatives thereof to an amino or amidocaproic acid product. The amino or amidocaproic acid product may then be converted to caprolactam. The present invention also includes products produced by such processes and products producable from such products.

30 Claims, No Drawings

(56) References Cited

OTHER PUBLICATIONS

Dangerfield et al., "Protecting-Group-Free Synthesis of Amines: Synthesis of Primary Amines from Aldehydes via Reductive Amination", The Journal of Organic Chemistry, vol. 75, No. 16, 2010, pp. 5470-5477.

Gervay-Hague et al., "Pyranosyl Sugar Amino Acid Conjugates: Their Biological Origins, Synthetic Preparations, and Structural Characterization", Journal of Carbohydrate Chemistry, vol. 21, No. 7-9, 2002, pp. 867-910.

Melvin et al., "The Improved Synthesis of β-D-glucuronides using TEMPO and t-butyl Hypochlorite", Tetrahedron Letters, vol. 40, 1999, pp. 1201-1202.

Ramachandrana et al., "Reductive Amination Using Ammonia Borane", Tetrahedron Letters, vol. 51, 2010, pp. 3167-3169.

Pandey et al., Positive Cooperativity in Non-Ionic Micellar Catalysed Oxidation of Aminoalcohols by N-Bromosuccinimide. A Kinetic Study, Oxidation Communications, vol. 29, No. 2, 2006, pp. 328-334.

International Preliminary Report on Patentability received for PCT Patent Application No. PCT/US2012/031284, issued on Oct. 15, 2013, 12 pages.

* cited by examiner

PRODUCTION OF CAPROLACTAM FROM CARBOHYDRATE-CONTAINING MATERIALS

CROSS-REFERENCE TO RELATED APPLICATION

This application claims the benefit under 35 U.S.C. §119(e) of U.S. Provisional Application No. 61/475,177, filed Apr. 13, 2011, which is hereby incorporated by reference in the present disclosure in its entirety.

BACKGROUND

I. Field

The present disclosure relates generally to processes for the chemocatalytic conversion of glucose to caprolactam; more specifically, it relates to chemocatalytic oxidation and reduction processes for the conversion of glucose to caprolactam.

II. Related Art

Caprolactam is a chemical intermediate primarily used in the production of nylon 6 fibers and resins.

Conventional caprolactam technology is based on the intermediate cyclohexanone, which is typically produced by the oxidation of cyclohexane but is also produced by the partial hydrogenation of phenol. For the production of caprolactam by either process, cyclohexanone is reacted with a hydroxylamine to produce cyclohexanone oxime followed by a Beckmann rearrangement of the oxime using oleum to yield caprolactam. One disadvantage of the above-described conventional technology is that large amounts of ammonium sulfate—up to 4.5 tons/ton of caprolactam—are produced. Over many years much of the development work directed to manufacturing caprolactam from cyclohexanone has been focused on reducing or even eliminating this byproduct. For example, DSM's HPO Plus™ process (Hydroxylamine Phosphate Oxime), now believed to be used for the production of about 30% of the world's caprolactam, has substantially reduced the quantity of ammonium salt byproduct by as much as two thirds on a ton of salt/ton of product basis. More recently, Sumitomo has commercialized a process that eliminates the production of ammonium sulfate. The process employs an "ammoximation" reaction, whereby cyclohexane is reacted with ammonia and hydrogen peroxide in the presence of a catalyst, and a gas-phase Beckmann rearrangement, see, for example U.S. Pat. Nos. 6,265,574, 6,462,235 and 4,745,221. Significantly, one drawback of this process is the cost of hydrogen peroxide.

Other routes, developed primarily in the 1990s, sought to manufacture caprolactam from butadiene or adiponitrile. DSM, working first with DuPont and thereafter with Shell, developed the Altam process, see, for example, WO 2002/083635, whereby butadiene and carbon monoxide are employed to make caprolactam without ammonium sulfate production. However, this process is still in the final phases of development and employs several complex catalytic reactions—carbonylation, hydroformylation, reductive amination, and cyclization. BASF and DuPont experimented with the production of caprolactam via adiponitrile, although it is not clear whether such processes are currently being practiced. See, for example, U.S. Pat. Nos. 6,372,939, 6,894,163, 6,521,779, and WO 2001/096294, Toray has developed a photochemical process to convert cyclohexane into cyclohexanone oxime in the presence of nitrosyl chloride and hydrogen chloride, bypassing the use of cyclohexanone or the oximation step. Although this process may provide capital savings, the photochemical process demands significantly more power and the development of large scale photochemical reactors. See Chapter devoted to caprolactam within *Kirk-Othmer Encyclopedia of Chemical Technology* 5th Edition, John Wiley and Sons 2001.

In addition to the above-mentioned shortcomings of the processes currently commercially employed (about 90% of the world's production of caprolactam is via cyclohexanone) and those being announced or developed as potentially viable alternatives, each of these processes suffers fundamentally from the increasing costs and volatility associated with the use of petroleum based feedstocks.

Thus, there remains a need for new, industrially scalable processes for the selective and commercially-meaningful conversion of a renewable feedstock, such as glucose derived from starch, cellulose, sucrose, or other carbohydrates to important chemical intermediates which may be converted to caprolactam.

SUMMARY

Briefly, therefore, the present invention is directed to processes for preparing caprolactam from glucose obtained from biorenewable materials. Generally, the process for preparing caprolactam from glucose comprises converting glucose to an aminated polyol substrate, more preferably an acylamidopolyol substrate, converting at least a portion of the aminated polyol substrate to an amido polyhydroxy acid substrate, converting at least a portion of the amido polyhydroxy acid substrate to an aminocaproic or amidocaproic acid product, and converting at least a portion of the amino or amidocaproic acid product to caprolactam.

In accordance with the present invention, applicants disclose a process for preparing an amidocaproic acid product, the process comprising: chemocatalytically converting an amidopolyol substrate to the amidocaproic acid product. In some embodiments, the step of chemocatalytically converting the amidopolyol substrate to the amidocaproic acid product comprises the step of chemocatalytically converting the amidopolyol substrate to an amido polyhydroxy acid substrate. In some embodiments, the step of chemocatalytically converting the amidopolyol substrate to the amidocaproic acid product comprises the step of chemocatalytically converting the amido polyhydroxy acid substrate to the amidocaproic acid product. In some embodiments, the step of chemocatalytically converting the amidopolyol substrate to the amido polyhydroxy acid substrate comprises a chemocatalytic oxidation reaction. In some embodiments, the step of chemocatalytically converting the amido polyhydroxy acid substrate to the amidocaproic acid product comprises a chemocatalytic reduction reaction. In some embodiments, the chemocatalytic oxidation reaction comprises reacting the amidopolyol substrate in the presence of a heterogeneous oxidation catalyst and a source of oxidant. In some embodiments, the chemocatalytic reduction reaction comprises reacting the amido polyhydroxy acid substrate with hydrogen in the presence of a hydrodeoxygenation catalyst and a source of halogen. The present invention also relates to an amidocaproic acid product produced at least in part by the processes of any of the previous embodiments, where applicable.

The present invention also relates to a process for preparing an amidocaproic acid product, the process comprising: chemocatalytically converting glucose to the amidocaproic acid product. The present invention also relates to a process for preparing a reaction product comprising amino and amidocaproic acid, the process comprising: chemocatalytically converting an amino or amido polyhydroxy acid substrate to the reaction product. The present invention also relates to a process for producing an amidocaproic acid product comprising a) converting glucose to an amidopolyol substrate, b) converting at least a portion of the amidopolyol substrate to an amido polyhydroxy acid substrate, and c) converting at least a portion of the amido polyhydroxy acid substrate to the amidocaproic acid product. In some embodiments, the converting at least a portion of the amidopolyol substrate to an amido polyhydroxy acid substrate comprises a chemocatalytic oxidation reaction. In some embodiments, the converting at least a portion of the amido polyhydroxy acid substrate to the amidocaproic acid product comprises a chemocatalytic reduction reaction. In some embodiments, the chemocatalytic oxidation reaction comprises reacting the amidopolyol substrate in the presence of a heterogeneous catalyst and a source of oxidant. In some embodiments, the chemocatalytic reduction reaction comprises reacting the amido polyhydroxy acid substrate with hydrogen in the presence of a hydrodeoxygenation catalyst and a source of halogen. The present invention also relates to an amidocaproic acid product produced at least in part by the processes of any of the previous embodiments, where applicable.

The present invention also relates to a process for producing caprolactam comprising a) converting glucose to an amidopolyol substrate, b) converting at least a portion of the amidopolyol substrate to an amido polyhydroxy acid substrate, c) converting at least a portion of the amido polyhydroxy acid substrate to an amidocaproic acid product, and d) converting at least a portion of the amidocaproic acid product to caprolactam. In some embodiments, the step of chemocatalytically converting the amidopolyol substrate to the amido polyhydroxy acid substrate comprises a chemocatalytic oxidation reaction. In some embodiments, the step of chemocatalytically converting the amido polyhydroxy acid substrate to the amidocaproic acid product comprises a chemocatalytic reduction reaction. In some embodiments, the chemocatalytic reduction reaction comprises reacting the amido polyhydroxy acid substrate with hydrogen in the presence of a hydrodeoxygenation catalyst and a source of halogen. The present invention also relates to caprolactam produced at least in part by the processes of any of the previous embodiments, where applicable.

The present invention also relates to a process for preparing an amido polyhydroxy acid product, the process comprising: reacting, in the presence of an oxidation catalyst, an amidopolyol substrate and an oxidant to convert at least a portion of the amidopolyol substrate to the amido polyhydroxy acid product, wherein the amidopolyol substrate comprises a compound of formula I and the amido polyhydroxy acid product comprises a compound of formula II:

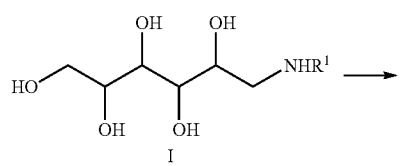

I

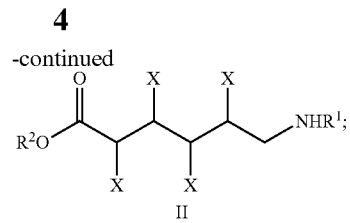

II wherein each X is independently, hydroxyl, oxo, or acyloxy;

wherein $R^1$ is acyl, substituted acyl, aroyl or substituted aroyl; and wherein $R^2$ is a salt-forming ion, hydrogen, or a lactone thereof. In some embodiments, each X is selected from the group of hydroxyl and hydrogen. In some embodiments, at least one X is hydroxyl. In some embodiments, $R^1$ is acetyl. In some embodiments, the amidopolyol substrate is 6-amido-6-deoxysorbitol or 6-N-acetamido-6-deoxysorbitol. In some embodiments, the amido polyhydroxy acid product is 6-N-acetamido-6-deoxygulonic acid. In some embodiments, the oxidation catalyst comprises a heterogeneous catalyst. In some embodiments, the oxidation catalyst comprises a metal selected from the group consisting of Pd and Pt. In some embodiments, the oxidation catalyst comprises at least one metal selected from the group of alkali and alkaline earth metals. In some embodiments, the oxidation catalyst is a supported catalyst and the catalyst support comprises a material selected from the group consisting of carbon, silica, titania, zirconia, montmorillonite and zeolite. In some embodiments, the reaction is maintained at a temperature of at least about 80° C. In some embodiments, the reaction is maintained at a temperature of about 60° C. to about 150° C. In some embodiments, the reaction is conducted under a partial pressure of oxygen in the range of from about 15 psia (104 kPa) to about 2000 psia (13790 kPa). In some embodiments, the reaction is conducted under a partial pressure of oxygen in the range of from about 75 psia (517 kPa) to about 1500 psia (10342 kPa). In some embodiments, the oxidant is supplied to the reaction as air, oxygen-enriched air, oxygen alone, or oxygen with one or more constituents substantially inert to the reaction. In some embodiments, at least a portion of the amidopolyol substrate is derived from glucose. In some embodiments, at least a portion of the glucose is obtained from a carbohydrate source. The present invention also relates to an amidopolyhydroxy acid product produced at least in part by the processes of any of the previous embodiments, where applicable.

The present invention also relates to a process for preparing an amino or amidocaproic acid product, the process comprising: reacting, in the presence of a hydrodeoxygenation catalyst and a halogen source, an amino or amido polyhydroxy acid substrate and hydrogen to convert at least a portion thereof to the amino or amidocaproic acid product, wherein the amino or amido polyhydroxy acid substrate is a compound of formula IIa and the amino or amidocaproic acid product is a compound of formula III:

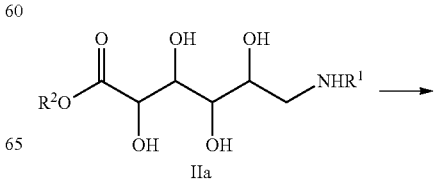

IIa

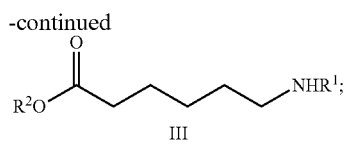

wherein each X is independently hydroxyl, oxo, halo, or acyloxy;

wherein R¹ is acyl, substituted acyl, aroyl, substituted aroyl or hydrogen; and wherein R² is a salt-forming ion, hydrogen, or a lactone thereof. In some embodiments, each X is hydroxyl. In some embodiments, R¹ is acyl. In some embodiments, R¹ is acetyl. In some embodiments, the amino or amido polyhydroxy acid substrate is 6-amino-6-deoxygulonic acid or 6-N-acetamino-6-deoxygulonic acid. In some embodiments, the amino or amido polyhydroxy acid substrate is 6-N-acetamido-6-deoxygulonic acid. In some embodiments, the hydrodeoxygenation catalyst comprises a heterogeneous catalyst. In some embodiments, the hydrodeoxygenation catalyst comprises at least a first metal selected from the group of palladium, iridium and rhodium. In some embodiments, the catalyst comprises a second metal selected from the group consisting of Ru, Rh, Pd, Pt, Ir and Au provided, however, the second metal is different than the first metal. In some embodiments, the hydrodeoxygenation catalyst comprises palladium and rhodium. In some embodiments, the hydrodeoxygenation catalyst is a supported catalyst and the support is selected from the group consisting of silicas and zirconias. In some embodiments, the halogen source is selected form the group of ionic, atomic and molecular forms of iodine and bromine. In some embodiments, the halogen source is hydrogen iodide or hydrogen bromide. In some embodiments, the halogen source is hydrogen iodide. In some embodiments, the molar ratio of halogen source to amino or amido polyhydroxy acid substrate is at least about 1. In some embodiments, the reaction is maintained at a temperature of at least about 80° C. In some embodiments, the reaction is maintained at a temperature of about 100° C. to about 200° C. In some embodiments, the reaction is maintained at a temperature of about 120-180° C. In some embodiments, the reaction is conducted under a partial pressure of hydrogen in the range of from about 15 psia (104 kPa) to about 2000 psia (13790 kPa). In some embodiments, the reaction is conducted under a partial pressure of hydrogen in the range of from about 300 psia (2069 kPa) to about 1500 psia (10342 kPa). In some embodiments, at least a portion of the polyhydroxy acid substrate is derived from glucose. In some embodiments, at least a portion of the glucose is derived from a carbohydrate source. In some embodiments, the reaction further comprises a weak carboxylic acid, and wherein at least a portion of the polyhydroxy acid substrate is solubilized with the weak carboxylic acid. In some embodiments, the pKa of the weak carboxylic acid is at least about 4.5. In some embodiments, the weak carboxylic acid is acetic acid. The present invention also relates to a process for preparing caprolactam, the process comprising: converting by chemocatalytic means an amino or amido polyhydroxy acid substrate to an amino or amidocaproic acid product; and, converting the amino or amidocaproic acid to caprolactam. The present invention also relates to an amino or amidocaproic acid product produced at least in part by the processes of any of the previous embodiments, where applicable.

The present invention also relates to a process for preparing caprolactam, the process comprising:

a) reacting, in the presence of a reductive amination catalyst, glucose with hydrogen and ammonia to convert at least a portion of the glucose to an amidopolyol compound;

b) reacting, in the presence of an oxidation catalyst, at least a portion of the amidopolyol compound and an oxidant to convert at least a portion of the amidopolyol compound to an amido polyhydroxy acid product;

c) reacting, in the presence of a hydrodeoxygenation catalyst and a halogen source, at least a portion of the amidopolyhydroxy acid product and hydrogen to convert at least a portion of the amido polyhydroxy acid product to an amidocaproic acid compound; and d) cyclizing at least a portion of the amidocaproic acid compound to produce caprolactam. In some embodiments, the cyclizing step is carried out chemocatalytically. In some embodiments, at least a portion of the glucose is obtained from a carbohydrate source. The present invention also relates to a process for preparing caprolactam, the process comprising: converting amino or amidogulonic acid to caprolactam. The present invention also relates to a process for preparing caprolactam, the process comprising: converting an amino or amidocaproic acid product to caprolactam, wherein the amino or amidocaproic acid product is prepared in accordance with any of the previous embodiments, where applicable. The present invention also relates to a process for producing caprolactam from glucose, the process comprising: converting glucose to amidocaproic acid and converting at least some of the amidocaproic acid to caprolactam. In some embodiments, the glucose is converted to an amido polyhydroxy acid product prior to the production of amidocaproic acid. The present invention also relates to an amido polyhyroxy acid product produced at least in part by the process of any of the previous embodiments, where applicable. In some embodiments, the amido polyhyroxy acid product is 6-N-acetamido-6-deoxygulonic acid. The present invention also relates to an amidocaproic acid product produced at least in part by the process of any of the previous embodiments, where applicable. In some embodiments, the amidocaproic acid product is 6-N-acetamidocaproic acid. The present invention also relates to caprolactam produced at least in part from an amido polyhydroxy acid product produced by the process of any of the previous embodiments, where applicable. The present invention also relates to caprolactam produced at least in part from an amino or amidocaproic acid product produced by the process of any of the previous embodiments, where applicable. The present invention also relates to caprolactam produced at least in part by the process of any of any of the previous embodiments, where applicable. The present invention also relates to a process for preparing nylon 6, the process comprising: converting caprolactam produced at least in part by the process of any of the previous embodiments, where applicable, into nylon 6.

The present invention also relates to a process for preparing an amidocaproic acid compound from glucose, the process comprising:

a) converting glucose to a cyclic amido polyol compound of formula IV:

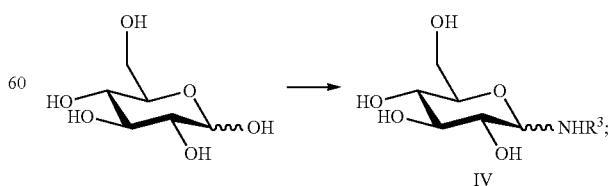

wherein R³ is acyl, substituted acyl, aroyl or substituted aroyl;

b) reacting, in the presence of an oxidation catalyst, at least a portion of the cyclic amido polyol compound and an oxidant to convert at least a portion of the cyclic amido polyol compound to a cyclic polyhydroxy acid compound of formula V:

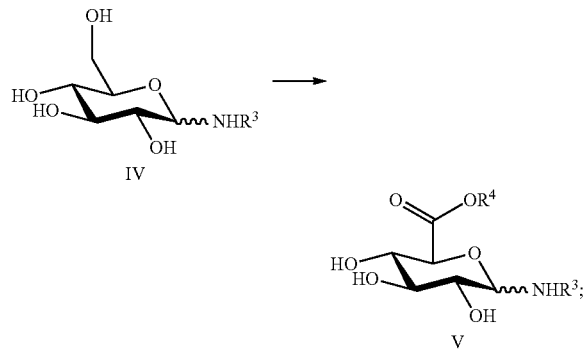

wherein $R^3$ is as defined above and $R^4$ is a salt-forming ion or hydrogen; and c) reacting, in the presence of a hydrodeoxygenation catalyst and a halogen source, at least a portion of the cyclic polyhydroxy acid compound and hydrogen to convert at least a portion of the cyclic polyhydroxy acid compound to an amidocaproic acid compound of formula VI:

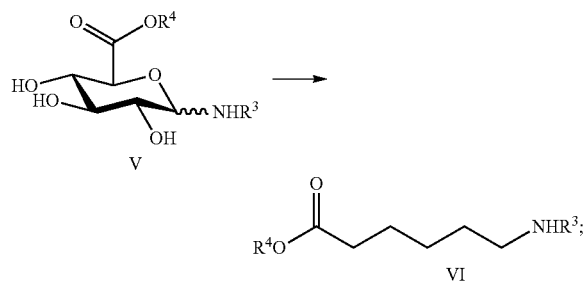

where $R^3$ and $R^4$ are as defined above. The present invention also relates to an amidocaproic acid compound produced at least in part by the processes of any of the previous embodiments, where applicable.

The present invention also relates to a process for producing caprolactam, the process comprising:

a) converting glucose to a cyclic amido polyol compound of formula IV:

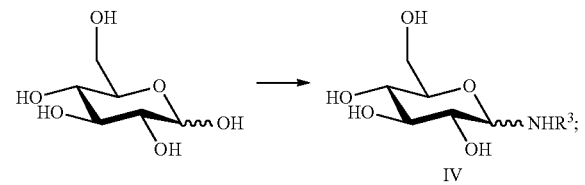

wherein $R^3$ is acyl, substituted acyl, aroyl or substituted aroyl;

b) reacting, in the presence of an oxidation catalyst, at least a portion of the cyclic amido polyol compound and an oxidant to convert at least a portion of the cyclic amido polyol compound to a cyclic polyhydroxy acid compound of formula V:

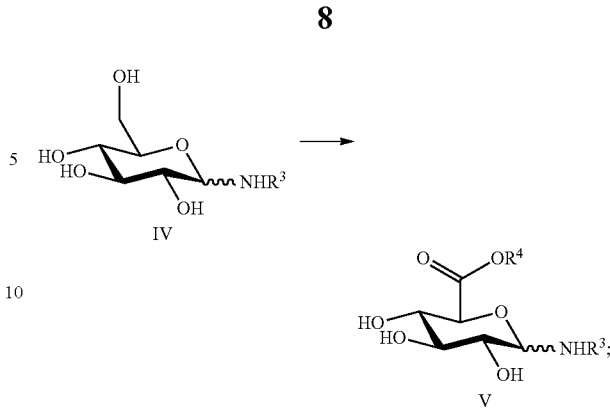

wherein $R^3$ is as defined above and $R^4$ is a salt-forming ion or hydrogen;

c) reacting, in the presence of a hydrodeoxygenation catalyst and a halogen source, at least a portion of the cyclic polyhydroxy acid compound and hydrogen to convert at least a portion of the cyclic polyhydroxy acid compound to an amidocaproic acid compound of formula VI:

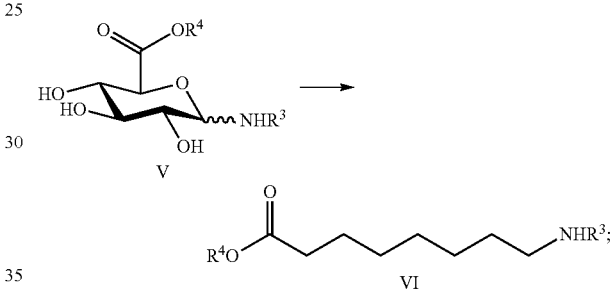

and d) cyclizing at least a portion of the amidocaproic acid compound to produce caprolactam. In some embodiments, the cyclizing step is carried out chemocatalytically. In some embodiments, at least a portion of the glucose is obtained from a carbohydrate source. The present invention also relates to an amidocaproic acid compound produced at least in part by the processes of any of the previous embodiments, where applicable. The present invention also relates to caprolactam produced at least in part by the process of any of the previous embodiments, where applicable.

The present invention also relates to a process for preparing caprolactam, the process comprising: a) reacting, in the presence of a reductive amination catalyst, glucose with hydrogen, ammonia and a weak carboxylic acid to convert at least a portion of the glucose to an acylamidopolyol compound; b) reacting, in the presence of an oxidation catalyst, at least a portion of the acylamidopolyol compound and an oxidant to convert at least a portion of the acylamidopolyol compound to an acylamidogulonic acid compound; c) reacting, in the presence of a hydrodeoxygenation catalyst and a halogen source, at least a portion of the acylamidogulonic acid compound and hydrogen to convert at least a portion of the acylamidogulonic acid compound to an acylamidocaproic acid compound; and d) deacylating and cyclizing at least a portion of the acylamidocaproic acid compound to produce caprolactam. In some embodiments, the acyl group is acetyl. In some embodiments, the process further comprises adding a weak carboxylic acid to step c). In some embodiments, the weak carboxylic acid is acetic acid. In any of the previous embodiments, where applicable, the step of converting glucose to the amidopolyol substrate comprises converting glucose to an aminopolyol and reacting the aminopolyol with a protecting molecule to convert the aminopolyol to an amidopolyol.

The present invention also relates to a process for preparing an amidocaproic acid product, the process comprising: reacting an aminopolyol substrate with a protecting molecule to produce an amidopolyol, and chemocatalytically converting the amidopolyol to amidocaproic acid product. In some embodiments, the protecting molecule is selected such that nitrogen of the aminopolyol is bonded to a functional group selected from the group consisting of acyl, substituted acyl, aryol, and substituted aroyl. In some embodiments, the protecting molecule is a monocarboxylic acid. In some embodiments, the protecting molecule is acetic acid.

The invention also relates to caprolactam produced at least in part by the process of any of the previous embodiments, where applicable.

The present invention also relates to a process for the production of caprolactam comprising: converting xylose to a polyhydroxy acid substrate; reacting the polyhydroxy acid substrate with a protecting molecule to produce an amido polyhydroxy acid substrate; chemocatalytically converting the amido polyhydroxyl acid substrate to an amidocaproic acid product; and converting the amidocaproic acid product to caprolactam.

DETAILED DESCRIPTION

The following description sets forth exemplary methods, parameters and the like. It should be recognized, however, that such description is not intended as a limitation on the scope of the present invention.

In accordance with the present invention, applicants disclose processes for the chemocatalytic conversion of a glucose source to caprolactam and intermediate processes and products along the pathway. Generally, the process for producing caprolactam includes converting glucose to an aminated polyol substrate, chemocatalytically converting the aminated polyol substrate to an amido polyhydroxy acid substrate, and chemocatalytically converting the amido polyhydroxy acid substrate to an amino or amidocaproic acid product. The amino or amidocaproic acid product can then be cyclized to produce caprolactam.

Further, in accordance with the present invention, applicants disclose processes for the catalytic oxidation of an aminated polyol substrate to an amidopolyhydroxy acid substrate. In more preferred embodiments, the catalytic oxidation includes reacting, in the presence of an oxidation catalyst (i.e., catalyst suitable for the oxidation reaction), an acylamidopolyol substrate and an oxidant to convert at least a portion of an acylamidopolyol substrate to acylamidogulonic acid.

The present invention also relates to processes for the catalytic hydrodeoxygenation of an amino or amido polyhydroxy acid substrate to an amino or amidocaproic acid product. The amino or amido polyhydroxy acid substrate preferably is amidogulonic acid and/or derivatives thereof. The catalytic hydrodeoxygenation includes reacting, in the presence of a hydrodeoxygenation catalyst (i.e., catalyst suitable for the hydrodeoxygenation reaction) and a halogen source, an amino or amido polyhydroxy acid substrate and hydrogen to convert at least a portion of the substrate to an amino or amidocaproic acid product.

In another aspect of the invention, the caprolactam prepared in accordance with the disclosed processes may be converted, according to processes known in the art, to various other industrially significant chemicals including nylon 6.

I. Feedstocks

Glucose can be obtained from various carbohydrate-containing sources including conventional biorenewable sources such as corn grain (maize), wheat, potato, cassava and rice as well as alternative sources such as energy crops, plant biomass, agricultural wastes, forestry residues, sugar processing residues and plant-derived household wastes. More generally, biorenewable sources that may be used in accordance with the present invention include any renewable organic matter that includes a source of carbohydrates such as, for example, switch grass, miscanthus, trees (hardwood and softwood), vegetation, and crop residues (e.g., bagasse and corn stover). Other sources can include, for example, waste materials (e.g., spent paper, green waste, municipal waste, etc.). Carbohydrates such as glucose may be isolated from biorenewable materials using methods that are known in the art. See, for example, Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006; Shang-Tian Yang, *Bioprocessing for Value-Added Products from Renewable Resources New Technologies and Applications*, Elsevier B. V. 2007; Furia, *Starch in the Food Industry*, Chapter 8, CRC Handbook of Food Additives 2nd Edition, CRC Press 1973. See also chapters devoted to Starch, Sugar and Syrups within Kirk-Othmer Encyclopedia of Chemical Technology 5th Edition, John Wiley and Sons 2001. Also, processes to convert starch to glucose are known in the art, see, for example, Schenck, "Glucose and Glucose containing Syrups" in *Ullmann's Encyclopedia of Industrial Chemistry*, Wiley-VCH 2009. Furthermore, methods to convert cellulose to glucose are known in the art, see, for example, Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006; Shang-Tian Yang, *Bioprocessing for Value-Added Products from Renewable Resources New Technologies and Applications*, Elsevier B. V. 2007.

II. Preparation of Aminated Polyols from Glucose

The preparation of aminated polyols can be effected with glucose using reductive amination methods that are generally known in the art. See, for example, U.S. Pat. No. 2,016,962, which illustrates a method for the preparation of glucosamines, such as glucamine, using a nickel catalyst in the presence of ammonia and hydrogen. Further examples of the preparation of aminopolyols using a nickel catalyst in the presence of ammonia and hydrogen include EP 0536939 and U.S. Pat. No. 6,429,335, where 1 deoxy-1-aminosorbitol was produced in up to 90 or 95% yield, respectively. Other reductive amination methods may also be employed, see for example, U.S. Pat. Nos. 6,365,778; 5,723,673; 5,625,098; 5,449,770; and 2,197,540; WO 1995/019951; WO 2008/006748; *J. Org. Chem*. Vol. 75, p. 5470-5477; *Anal. Bioanal. Chem*. Vol. 381, p. 1130-1137 (2005); *Tetrahedron Lett*., Vol. 51, p. 3167-3169 (2010); and Fasche, Valot, and Lemeaire, *Fine Chemicals through Heterogeneous Catalysis*, Wiley-VCH 2001, p. 461-462.

In more preferred embodiments of the process of the present invention, the nitrogen of the aminated polyol is protected by being bonded to the carbon of a carbonyl-containing group, such as an acyl or aroyl containing group, to form, for example, an acyl or aroylamidopolyol compound. In certain preferred embodiments, an acyl or aroylamidopolyol compound may be formed directly from glucose using reductive amination in the presence of an amine protecting molecule such as, for example, acetic acid, formic acid or benzoic acid. See for example, F. Fasche, Valot, F. and Lemeaire, M in Fine Chemicals through Heterogeneous Catalysis Wiley-VCH 2001 p 461-2. As used herein, the term "acyl" encompasses groups comprising an alkyl, alkenyl, alkynyl, aryl or arylalkyl radical attached at one of the two available valence positions of a carbonyl carbon atom. Acyl groups are bonded to the nitrogen to which they are attached through the remaining open valence of the carbonyl carbon atom. More specifically, C1-C8 acyl groups include, for example, formyl, acetyl or pivaloyl. The hydrocarbyl groups that comprise an acyl group can be substituted with the substituents described herein as generally suitable substituents for each corresponding component of the acyl group. In various more preferred embodiments, the acyl group is an acetyl group. As used herein, the term "aroyl" includes, for example, benzoyl groups.

III. Preparation of an Amido Polyhydroxy Acid Substrate

The preparation of an amido polyhydroxy acid substrate, such as amidogulonic acid, can be effected by oxidation of aminopolyols using oxidation methods generally known in the art. See, for example, *Catalysis Today* Vol. 72, p. 43-49 (2002); JP 2003267939; *J. Biochem. J.* Vol. 68, p. 617-621 (1958); *Oxidation Communications*, Vol. 29, p. 328-334 (2006); US 20070299269; U.S. Pat. No. 7,439,388; *Tetrahedron Lett.* Vol. 40, p. 1201-1202 (1999); and *J. Carbohydrate Chem.* Vol. 21, p. 867-910 (2002). However, these methods suffer from economic shortcomings resulting from, among other matters, process yield limitations and the requirement for additional reaction constituents.

Applicants have discovered that amidopolyol substrates of formula I may be converted to an amidopolyhydroxy acid substrate of formula II in high yield by reacting the amidopolyol substrate with oxygen (as used herein, oxygen can be supplied to the reaction as air, oxygen-enriched air, oxygen alone, or oxygen with other constituents substantially inert to the reaction) in the presence of an oxidation catalyst according to the following reaction:

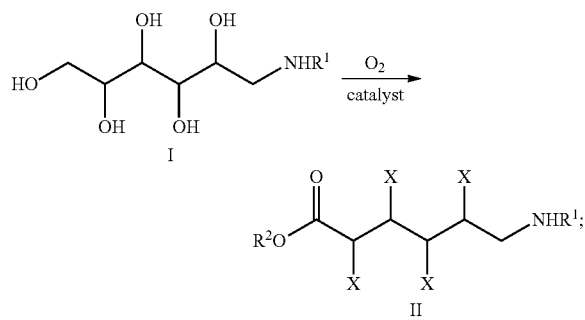

wherein each X is independently, hydroxyl, oxo, or acyloxy; $R^1$ is acyl, substituted acyl, aroyl or substituted aroyl; and $R^2$ is a salt-forming ion, hydrogen, or a lactone thereof.

Salt forming ions include, without limitation, for example, metal ions (e.g., alkali and alkaline earth metals). When $R^2$ is a salt forming ion (i.e., a cation), the carboxyl group may be considered to be an anion (i.e., carboxylate anion).

In various preferred embodiments, the amido polyhydroxy acid substrate comprises a compound of formula II, wherein each X is hydroxyl and $R^2$ is a salt forming ion or hydrogen and R1 is acyl, more preferably acetyl.

As shown in formulas I and II, the amidopolyol substrate and the amido polyhydroxy acid substrate each contain a six carbon chain comprising four chiral centers. As a result, several stereoisomers are possible. However, the preferred amidopolyol substrate comprises amidosorbitol and even more preferably comprises acetamidosorbitol, and the preferred amido polyhydroxy acid substrate comprises acetamidogulonic acid. The amidopolyhydroxy acid substrate may comprise various lactones derived from, for example, amidogulonic acid. For example, not wishing to be bound by theory, it is believed that various lactones are present in equilibrium with the amido polyhydroxy acid in aqueous solution and may be isolated therefrom using appropriate conditions.

Generally, the temperature of the oxidation reaction mixture is at least about 40° C., more typically 60° C., or higher. In various embodiments, the temperature of the oxidation reaction mixture is from about 40° C. to about 150° C., from about 60° C. to about 150° C. or from about 80° C. or about 150° C.

Typically, the partial pressure of oxygen is at least about 15 pounds per square inch absolute (psia) (104 kPa), at least about 25 psia (172 kPa), at least about 40 psia (276 kPa), or at least about 60 psia (414 kPa). In various embodiments, the partial pressure of oxygen is up to about 2000 psia (13790 kPa), or more, typically in the range of from about 75 psia (517 kPa) to about 1500 psia (10342 kPa).

In general, the oxidation reaction can be conducted in a batch, semi-batch, or continuous reactor design using fixed bed reactors, trickle bed reactors, slurry phase reactors, moving bed reactors, or any other design that allows for heterogeneous catalytic reactions. Examples of reactors can be seen in *Chemical Process Equipment—Selection and Design*, Couper et al., Elsevier 1990, which is incorporated herein by reference. It should be understood that the aminopolyol substrate, oxygen, any solvent or combination of solvents, and the oxidation catalyst may be introduced into a suitable reactor separately or in various combinations.

Catalysts suitable for the oxidation reaction ("oxidation catalyst") include heterogeneous catalysts, including solid-phase catalysts with one or more supported or unsupported metals. In various embodiments, the metal is present at a surface of a support (i.e., at one or more surfaces, external or internal). Typically, the catalyst comprises metal selected from the group consisting of palladium, platinum, and combinations thereof. Additional other metals may be present, including one or more alkali or alkaline earth metals alone or in combination with other metals such as one or more d-block metals, one or more rare earth metals (e.g. lanthanides), and/ or one or more main group metals (e.g. Ga, Tl, In, Sn, Pb or Bi). In general, the metals may be present in various forms (e.g., elemental, metal oxide, metal hydroxides, metal ions, etc.). Typically, the metal(s) at a surface of a support may constitute from about 0.25% to about 10%, or from about 1% to about 8%, or from about 1% to about 5% (e.g., about 2%) of the total weight of the catalyst.

In various embodiments, the oxidation catalyst comprises a first metal (M1) and an alkali or alkaline earth metal (M2) at a surface of a support, wherein the M1 metal is selected from the group consisting of palladium and platinum and the M2 is, in certain preferred embodiments, selected from Li, Na, K, Ru, Mg and Ca.

The M1:M2 molar ratio may vary. For example, the molar ratio of M1:M2 may range from about 1:100 to about 1:1 from about 1:100 to about 1:5, or from about 1:100 to about 1:10. In various preferred embodiments, the M1:M2 molar ratio may vary, for example, from about 1:100 to about 1:10, from about 3:1 to about 1:1, or from about 1:100 to about 1:20.

Moreover, the weight percents of M1 and M2 relative to the catalyst weight may vary. Typically, the weight percent of M1 may range from about 0.25% to about 10%, more preferably from about 1% to about 8%, and still more preferably from about 0.5% to about 1.5% (e.g., about 0.5-1%). The weight percent of M2 may range from about 0.001% to about 20%, from about 0.01% to about 20%, or from about 0.01% to about 10%, and still more preferably from about 0.01% to about 5%.

Suitable catalyst supports include carbon, alumina, silica, ceria, titania, zirconia, niobia, zeolites (preferably, Y, ZSM 5, MWW and beta), molecular sieves, magnesia, clays, iron oxide, silicon carbide, aluminosilicates, and modifications, mixtures or combinations thereof. The preferred support materials may be modified using methods known in the art such as heat treatment, acid treatment, steam treatment or by the introduction of a dopant (for example, metal-doped titanias, metal-doped zirconias (e.g., tungstated-zirconia), metal-doped cerias, and metal-modified niobias). Particularly preferred supports are carbon (which may be activated carbon, carbon black, coke or charcoal), zirconia, titania, zeolites and silica. The catalyst support may be treated so as to promote the preferential deposition of metal on the outer surface of the support so as to create a shell type catalyst. The supports may be in a variety of forms, such as powders, pellets, spheres, extrudates and xerogels.

When a catalyst support is used, the metals may be deposited using procedures known in the art including, but not limited to incipient wetness, ion-exchange, deposition-precipitation, and vacuum impregnation. When two or more metals are deposited on the same support, they may be deposited sequentially or simultaneously. In various embodiments, following metal deposition, the catalyst is dried at a temperature of at least about 50° C., more typically at least about 120° C. for a period of time of at least about 1 hour, more typically 3 hours or more. In these and other embodiments, the catalyst is dried under sub-atmospheric pressure conditions. In various embodiments, the catalyst is reduced after drying (e.g., by flowing 5% $H_2$ in $N_2$ at 350° C. for 3 hours). Still further, in these and other embodiments, the catalyst is calcined, for example, at a temperature of up to about 500° C. for a period of time (e.g., at least about 3 hours).

The reaction product of the oxidation step will yield, as described above, an amido polyhydroxy acid substrate in considerable fraction, but may also yield derivatives thereof, such as one or more lactones derived therefrom. These acids (and derivatives thereof, such as the lactones) constitute a hydrodeoxygenation substrate which is particularly amenable to the production of an amino or amidocaproic acid compound as hereinafter described. One advantage of higher concentrations of lactones derived from the amido polyhydroxy acid product may be further improvement in the economics of the hydrodeoxygenation step resulting from a reduction in the amount of water in the reaction.

The amido polyhydroxy acid substrate may be recovered from the oxidation reaction mixture by one or more conventional methods known in the art including, for example, solvent extraction, crystallization or evaporative processes.

IV. Preparation of an Amino or Amidocaproic Acid Product

Applicants have discovered that an amino or amidocaproic acid product may be prepared by a chemocatalytic conversion of amino or amido polyhydroxy acid substrate under particular hydrodeoxygenation conditions as hereinafter described. The amido polyhydroxy acid substrate, from which an amino or amidocaproic acid product can be produced, is preferably produced by the processes above described. The aminocaproic acid product can be produced from an amino polyhydroxy acid substrate in accordance with the hydrodeoxygenation conditions as hereinafter described.

The amino or amido polyhydroxy acid substrate includes compounds of the formula IIa:

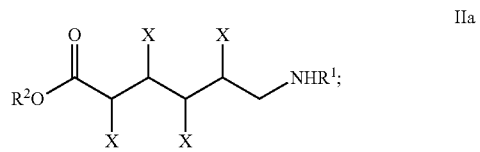

wherein the amido polyhydroxy acid substrate is defined by the above formula when each X is independently hydroxyl, oxo, halo, or acyloxy, $R^1$ is acyl, substituted acyl, aroyl or substituted aroyl, and $R^2$ is a salt-forming ion, hydrogen, or a lactone thereof; and wherein the amino polyhydroxy acid substrate is defined by the above formula when each X is independently hydroxyl, oxo, halo, or acyloxy; $R^1$ is hydrogen; and $R^2$ is a salt-forming ion, hydrogen, or a lactone. Salt-forming ions can include, for example, the hydrohalide salts, such as hydrobromide or hydroiodide, of the polyhydroxy acid substrate.

As shown in formula IIa, the amino or amido polyhydroxy acid substrate contains a six carbon chain comprising four chiral centers. As a result several stereoisomers are possible including amino or amidogulonic acid compounds and amino or amidogluconic acid compounds. However, a particularly preferred substrate for the production of caprolactam in accordance with the present invention is acylamidogulonic acid compound; more preferably, acetamidogulonic acid and/or derivatives thereof (such as, for example, lactones).

In accordance with various embodiments for the production of caprolactam, an amidocaproic acid product (formula III, below) is prepared by reacting, in the presence of a hydrodeoxygenation catalyst and a halogen source, an amido polyhydroxy acid substrate (formula IIa) and hydrogen, according to the following reaction:

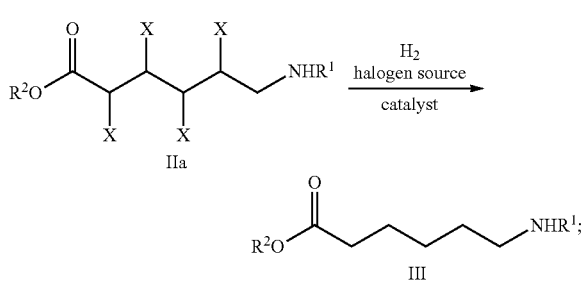

wherein X, $R^1$, and $R^2$ are defined as described above with respect to an amido polyhydroxy acid substrate.

In preferred embodiments, the amidocaproic acid product comprises 6-amidocaproic acid or, more preferably, 6-N-acetamidocaproic acid. In such embodiments, the polyhydroxy acid substrate comprising amidogulonic acid is converted to amidocaproic acid product by catalytic hydrodeoxygenation, wherein the carbon-X groups are converted to carbon-hydrogen groups.

In accordance with various embodiments for the production of caprolactam, an aminocaproic acid product (formula IIIa) is prepared by reacting, in the presence of a hydrodeoxygenation catalyst and a halogen source, an amino polyhydroxy acid substrate (formula IIa) and hydrogen, according to the following reaction:

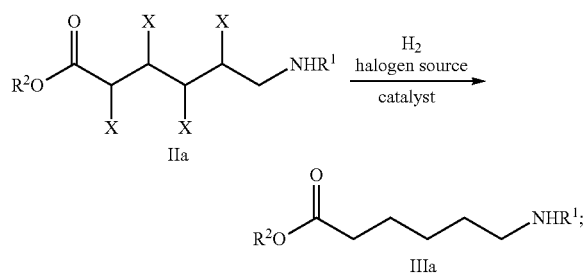

wherein R¹ is acyl or hydrogen, and X and R² are defined as described above with respect to an amino polyhydroxy acid substrate of Formula IIa provided, however, if R¹ is hydrogen the reaction product is an aminocaproic acid product, and if R¹ is acyl the reaction product can be amidocaproic acid product or a mixture of amino and amidocaproic acid product.

It should be recognized that the hydrodeoxygenation reaction can be conducted by first forming and optionally purifying or isolating various intermediates formed by, for example, combining an amino or amido polyhydroxy acid substrate and a halogen source and subsequently reacting the intermediate with hydrogen in the presence of the hydrodeoxygenation catalyst and optionally in the absence of any additional halogen source.

The halogen source may be in a form selected from the group consisting of atomic, ionic, molecular, and mixtures thereof. Halogen sources include bromine and iodine and the hydrohalic acids HBr and/or HI, or halide salts or (substituted or unsubstituted) alkyl halides thereof. In more preferred embodiments, the halogen source is hydrogen iodide or hydrogen bromide.

The molar ratio of halogen to amino or amido polyhydroxy acid substrate is generally about equal to, or greater than about, 1.

Generally, the reaction involving the polyhydroxy acid substrate conversion to an amino and/or amidocaproic acid product allows for recovery of the halogen source and catalytic quantities of halogen can be used, recovered and recycled for continued use as a halogen source.

Generally, the temperature of the hydrodeoxygenation reaction mixture is at least about 20° C., typically at least about 80° C., and more typically at least about 100° C. In various embodiments, the temperature of the hydrodeoxygenation reaction is conducted in the range of from about 20° C. to about 250° C., from about 100° C. to about 200° C., more preferably from about 120° C. to about 180° C.

Typically, the partial pressure of hydrogen is at least about 15 pounds per square inch absolute (psia) (104 kPa), at least about 25 psia (172 kPa), at least about 40 psia (276 kPa), or at least about 60 psia (414 kPa). In various embodiments, the partial pressure of hydrogen is up to about 2000 psia (13790 kPa), or more, typically in the range of from about 300 psia (2069 kPa) to about 1500 psia (10342 kPa).

The hydrodeoxygenation reaction is typically conducted in the presence of a solvent. Solvents suitable for the selective hydrodeoxygenation reaction include water and carboxylic acids, amides, esters, lactones, sulfoxides, sulfones and mixtures thereof. Preferred solvents include weak carboxylic acid (i.e., carboxylic acids having a pKa greater than about 3.5). A preferred weak carboxylic acid is acetic acid.

In general, the reaction can be conducted in a batch, semi-batch, or continuous reactor design using fixed bed reactors, trickle bed reactors, slurry phase reactors, moving bed reactors, or any other design that allows for heterogeneous catalytic reactions. Examples of reactors can be seen in *Chemical Process Equipment—Selection and Design*, Couper et al., Elsevier 1990, which is incorporated herein by reference. It should be understood that the amino or amido polyhydroxy acid substrate, halogen source, hydrogen, any solvent, and the hydrodeoxygenation catalyst may be introduced into a suitable reactor separately or in various combinations.

In various preferred embodiments, the hydrodeoxygenation catalyst is heterogeneous, but a suitable homogeneous catalyst may be employed. In these and various other preferred embodiments the hydrodeoxygenation catalyst comprises a solid-phase heterogeneous catalyst in which one or more metals is present at a surface of a support (i.e., at one or more surfaces, external or internal). Preferred metals are d-block metals which may be used alone, in combination with each other, in combination with one or more rare earth metals (e.g. lanthanides), and in combination with one or more main group metals (e.g., Ga, Tl, In, Sn, Pb or Bi). Preferred catalyst comprises palladium, iridium or rhodium. In general, the metals may be present in various forms (e.g., elemental, metal oxide, metal hydroxides, metal ions etc.). Typically, the metal (s) at a surface of a support may constitute from about 0.25% to about 10%, or from about 1% to about 8%, or from about 1.0% to about 7.5% (e.g., about 1-5%) of the catalyst weight.

In various embodiments, the hydrodeoxygenation catalyst comprises two or more metals. For example, two of more metals (M1 and M2) may be co-supported on or within the same support (e.g., as a mixed-metal catalyst on silica; M1/M2/silica catalyst), or they may be supported on different support materials. In various embodiments the hydrodeoxygenation catalyst comprises a first metal (M1) and a second metal (M2) at a surface of a support, wherein the M1 metal comprises a d-block metal and the M2 metal is selected from the group consisting of d-block metals, rare earth metals, and main group metals, wherein the M1 metal is not the same metal as the M2 metal. In various embodiments, the M1 metal is selected from the group consisting of rhodium, palladium and iridium. In various embodiments, the M2 metal is selected from the group consisting of titanium, vanadium, chromium, manganese, iron, cobalt, nickel, copper, molybdenum, ruthenium, rhodium, palladium, silver, tungsten, iridium, platinum, and gold. In more preferred embodiments, the M2 metal is selected from the group consisting of ruthenium, rhodium and iridium, platinum, and gold. In certain more preferred embodiments, M1 is palladium and M2 is rhodium.

In various embodiments, the M1:M2 molar ratio may vary, for example, from about 50:1 to about 1:1, from about 25:1 to about 1:1, from about 10:1 to about 1:1, from about 5:1 to about 1:1, from about 2:1 to about 1:1, or from about 1:1 to about 1:1. In various other embodiments, the M1:M2 molar ratio may vary, for example, from about 1:5 to about 1:1, or from about 1:2 to about 1:1.

Moreover, in various embodiments, the weight percents of M1 and M2 relative to the total catalyst weight may vary. Typically, the weight percent of M1 may range from about 0.5% to about 10%, more preferably from about 0.5% to about 8%, and still more preferably from about 0.51% to about 2% (e.g., about 1%). The weight percent of M2 may range from about 0.25% to about 3%, from about 0.25% to about 2%, or from about 0.25% to about 1%.

In various other embodiments, a third metal (M3) may be added to produce a M1/M2/M3 catalyst wherein the M3 metal is not the same metal as the M1 metal and the M2 metal. A preferred M3 is platinum or iridium.

Preferred catalyst supports include carbon, alumina, silica, ceria, titania, zirconia, niobia, zeolite, molecular sieves, magnesia, clays, iron oxide, silicon carbide, aluminosilicates, and modifications, mixtures or combinations thereof. The preferred supports may be modified through methods known in the art such as heat treatment, acid treatment, the introduction of a dopant (for example, metal-doped titanias, metal-doped zirconias (e.g. tungstated zirconia), metal-doped cerias, and metal-modified niobias). In various preferred embodiments, the hydrodeoxygenation catalyst support is selected from the group consisting of silica, zirconia and titania. In certain preferred embodiments, the catalyst comprises at least one of palladium, platinum, iridium and rhodium on a support comprising silica or zirconia.

When a catalyst support is used, the metals may be deposited using procedures known in the art including, but not limited to incipient wetness, ion-exchange, deposition-precipitation and vacuum impregnation. When the two or more metals are deposited on the same support, they may be deposited sequentially, or simultaneously. In various embodiments, following metal deposition, the catalyst is dried at a temperature of at least about 50° C., more typically at least about 120° C. or more for a period of time of at least about 1 hour, more typically at least about 3 hours or more. In some embodiments, catalyst is dried at a temperature of at least about 120° C. or more for a period of time of at least 12 hours or more. In these and other embodiments, the catalyst is dried under sub-atmospheric conditions. In various embodiments, the catalyst is reduced after drying (e.g., by flowing 5% $H_2$ in $N_2$ at 350° C. for 3 hours). Still further, in these and other embodiments, the catalyst is calcined, for example, at a temperature of at least about 500° C. for a period of time (e.g., at least about 3 hours).

Without being bound by theory not expressly recited in the claims, catalysts mixtures (co-catalysts or mixed metal catalysts) containing more than one metal may affect separate steps of the mechanistic reaction pathway.

The amido or aminocaproic acid product may be recovered from the hydrodeoxygenation reaction mixture by one or more conventional methods known in the art including, for example, solvent extraction, crystallization or evaporative processes.

V. Preparation of Caprolactam

The preparation of caprolactam from the acylamidocaproic acid product discussed hereinabove can be effected by cyclizing the acylamidocaproic acid product using methods generally known in the art. See, for example, WO 2010/041943 which illustrates the conversion of N-acylamidocaproic acid to caprolactam in high yields either chemocatalytically or biocatalytically. In preferred embodiments, wherein the amidocaproic acid product is a N-acylamidocaproic acid, the acid is deacylated and cyclized to form caprolactam. See, for example Green, T. W., Protecting Groups in Organic Synthesis 2$^{nd}$ Ed., Wiley and Sons 1991, p. 348, which illustrates that the deacylation of acylamines to form amines is a facile transformation. In embodiments wherein the hydrodeoxygenation reaction results in an aminocaproic acid product, a deacylation step is not required, and caprolactam may be isolated from the product of the selective cyclization of, for example, 6-aminocaproic acid.

In one embodiment of the present invention, caprolactam may be prepared by a) reacting, in the presence of a reductive amination catalyst, glucose with hydrogen and ammonia to convert at least a portion of the glucose to an aminopolyol compound; b) reacting the aminopolyol compound with a protecting molecule to convert at least a portion of the aminopolyol compound to an amidopolyol compound; c) reacting, in the presence of an oxidation catalyst, at least a portion of the amidopolyol compound and an oxidant to convert at least a portion of the amidopolyol compound to a amino polyhydroxy acid substrate; d) reacting, in the presence of a hydrodeoxygenation catalyst and a halogen source, at least a portion of the amido polyhydroxy acid substrate and hydrogen to convert at least a portion of the amido polyhydroxy acid substrate to an amidocaproic acid product; and e) converting at least a portion of the amidocaproic acid compound to caprolactam. It should be understood that steps a) and b) could be conducted as a single step in which, for example, glucose is converted to N-acetaminosorbitol by reacting, in a single reactor, glucose, hydrogen, an ammonia source and acetic acid; alternatively, of course, the ammonia and acetic acid could be present as an acetamide.

In an alternate embodiment, caprolactam may be prepared from glucose by conserving the cyclic glucose structure until a hydrodeoxygenation reaction is undertaken. In such a process, a hydrogen source would first be added as a reaction constituent to the hydrodeoxygenation reaction. The process includes:

a) chemocatalytically converting at least a portion of glucose to a cyclic amino or amido polyol compound of formula IV:

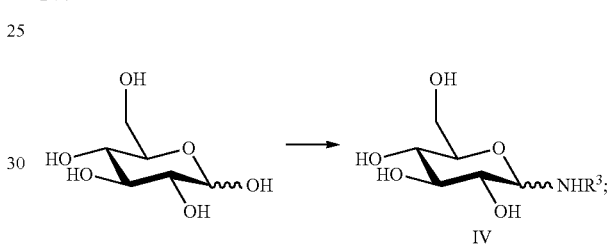

wherein $R^3$ is acyl, substituted acyl, aroyl, substituted aroyl, lactone or hydrogen;

b) reacting, in the presence of an oxidation catalyst, at least a portion of the cyclic amido polyol compound and an oxidant to convert at least a portion of the cyclic amido polyol compound to a cyclic amido polyhydroxy acid compound of formula V:

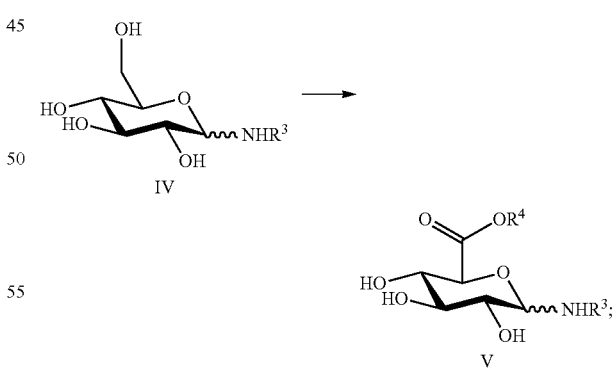

wherein $R^3$ is as defined above and $R^4$ is a salt-forming ion or hydrogen;

c) reacting, in the presence of a hydrodeoxygenation catalyst and a halogen source, at least a portion of the cyclic amido polyhydroxy acid compound and hydrogen to convert at least a portion of the cyclic amido polyhydroxy acid compound to an amidocaproic acid compound of formula VI:

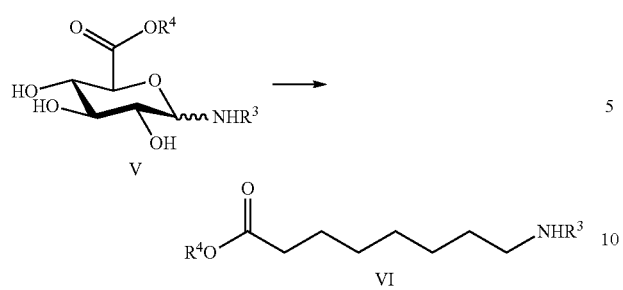

wherein R³ and R⁴ are as defined above; and d) converting at least a portion of the amidocaproic acid compound to produce caprolactam.

Yet another embodiment for the production of caprolactam comprises converting xylose to a polyhydroxy acid substrate, followed by amidation in the presence of, for example, acetic acid to produce an amido polyhydroxy acid substrate, which substrate is subsequently converted by hydrodeoxygenation to an amido caproic acid product which product is then converted by, for example, cyclization, to caprolactam. The process for converting the xylose to the polyhydroxy acid substrate entails carbohydrate chain extension chemistry; more specifically, Xylose+HCN can be reacted via a Fische-Kiliani reaction to produce gulose. (See, for example, Journal of Biological Chemistry (1918), 36, 347-9.) Gulose can then be subjected to amidation in the presence of, for example, acetic acid to produce acetamidogulose, and the acetamidogulose is then oxidized to produce acetamidogulonic acid. As described hereinabove, the acetamidogulonic acid can be converted by the hydrodeoxygenation reaction described heretofore with respect to amido polyhydroxy acid substrates to produce amidocaproic acid which, in turn, can be cyclized to produced caprolactam.

VI. Downstream Chemical Products

Caprolactam formed by the processes described herein can be further used for the preparation of polyamides by means generally known in the art. Specifically, caprolactam can be further used for the preparation of nylon 6. See, for example Kohan, Mestemacher, Pagilagan, Redmond, "Polyamides" in *Ullmann's Encyclopedia of Industrial Chemistry*, Wiley-VCH, Weinheim, 2005.

When introducing elements of the present invention or the preferred embodiments(s) thereof, the articles "a", "an", "the" and "said" are intended to mean that there are one or more of the elements. The terms "comprising", "including" and "having" are not intended to be inclusive and use of such terms mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

EXAMPLES

The following non-limiting examples are provided to further illustrate the present invention.

A. Preparation of Amidogulonic Acid

Experiment Protocol

Catalyst (ca. 8 mg) was weighed into a glass vial insert followed by addition of an aqueous acetaminosorbitol solution (250 µl of 0.25 M). The glass vial insert was loaded into a reactor and the reactor was closed. The atmosphere in the reactor was replaced with oxygen and pressurized to 75 psig at room temperature. Reactor was heated to 90° C. and maintained at 90° C. for 5 hours while shaking. After 5 hours, shaking was stopped and reactor was cooled to 40° C. Pressure in the reactor was then slowly released. The glass vial insert was removed from the reactor and centrifuged. The clear solution was diluted with deionized water and analyzed by ion chromatography with conductivity and Corona CAD detection.

Example 1

Suitably concentrated aqueous solutions of $Pt(NO_3)_2$ were added to ~0.5-2 g of an appropriate support and agitated to impregnate the supports. The samples were dried in an oven at 60-120° C. overnight under a dry air purge. Ca. 8 mg of solid were transferred into glass vials, and then reduced at 350° C. under forming gas (5% $H_2$ and 95% $N_2$) atmosphere for 3 hours with 5° C./min temperature ramp rate. The final catalysts were composed of ca. 4.0 wt. % Pt. Some examples below include the use of Zeolite supports from Zeolyst which were treated with an aqueous 0.5M $Na_2CO_3$ solution (adjusted to pH 10 with acetic acid), washed with deionized water and dried at 120° C. prior to use within impregnation experiments above. These catalysts were tested for acetamidosorbitol oxidation using the catalyst testing protocol and results are summarized in Table 1, below.

TABLE 1

| Entry | Catalyst Amt. (ma) | Support | Supplier | Acetamidosorbitol Conversion (%) | Acetamidogulonic Acid Yield (%) |
|---|---|---|---|---|---|
| 1 | 8 | Zeolite CBV 720 (Na) | Zeolyst | 93 | 71 |
| 2 | 8 | Zeolite CBV 780 (Na) | Zeolyst | 92 | 70 |
| 3 | 9 | Silica T-869 | Süd-chemie | 85 | 64 |
| 4 | 8 | Carbon HP-160 | Degussa | 81 | 64 |
| 5 | 9 | Silica Cariact G-6 | Fuji Silysia | 79 | 59 |
| 6 | 8 | Alumina SA 3132 | Saint-Gobain | 86 | 58 |
| 7 | 8 | Silica Cariact Q-6 | Fuji Silysia | 76 | 57 |
| 8 | 9 | Silica Davicat SI 1301 | Grace Davison | 86 | 57 |
| 9 | 8 | Silica Davisil 635 | Sigma-Aldrich | 80 | 56 |

TABLE 1-continued

| Entry | Catalyst Amt. (ma) | Support | Supplier | Acetamidosorbitol Conversion (%) | Acetamidogulonic Acid Yield (%) |
|---|---|---|---|---|---|
| 10 | 9 | Silica SS 61138 | Saint-Gobain | 85 | 56 |
| 11 | 7 | Carbon Supersorbon IV | Donau | 82 | 56 |
| 12 | 9 | Silica Cariact Q-10 | Fuji Silysia | 85 | 55 |
| 13 | 8 | Silica Merck 10180 | Merck | 82 | 55 |
| 14 | 8 | Silica Cariact G-10 | Fuji Silysia | 83 | 55 |
| 15 | 8 | Zeolite CP 814E (Na) | Zeolyst | 93 | 55 |
| 16 | 8 | Montmorillonite KA-3 | Süd-chemie | 82 | 54 |
| 17 | 9 | Zeolite CBV 5524G (Na) | Zeolyst | 89 | 54 |
| 18 | 8 | Alumina Davicat AL 2100 | Grace | 73 | 54 |
| 19 | 9 | Montmorillonite KA-160 | Süd-chemie | 80 | 53 |
| 20 | 9 | Zeolite CP 811C-300 (H) | Zeolyst | 73 | 52 |
| 21 | 8 | Silica Davicat SI 1302 | Grace Davison | 85 | 52 |
| 22 | 8 | Silica-Titania Cariact | Fuji Silysia | 75 | 52 |
| 23 | 8 | Silica SS 61137 | Saint-Gobain | 85 | 50 |
| 24 | 10 | Carbon SX Ultra Cat | Norit | 81 | 50 |

Example 2

250 μl of an aqueous solution of $HAuCl_4$ (containing 22.54 wt. % Au) was added to a 500 ml round bottom flask containing 400 ml of deionized water. 2.44 g of urea was added to the yellow solution, and stirred for 30 min. 4 g Titania P25 (Acros Organics) was then added to the solution and the resulting suspension heated to 80° C. and stirred for 72 hours. The resulting suspension was then centrifuged and supernatant was decanted. After residual liquid was removed the light yellow solid was dried in a 60° C. oven overnight under a dry air purge.

105 μl of an aqueous solution of $Pt(NO_3)_2$ (containing 12.9 wt. % Pt) was added to 0.5 g of the above solid and the mixture was agitated to impregnate the Au-containing support. The sample was dried in a 60° C. oven overnight under a dry air purge. The sample was then reduced at 350° C. under forming gas (5% $H_2$ and 95% $N_2$) atmosphere for 3 hours with 5° C./min temperature ramp rate. The final catalyst was composed of ca. 2.0 wt % Au and 4.0 wt % Pt. This catalyst was tested for acetamidosorbitol oxidation using the above described experiment protocol and results are summarized in Table 2.

TABLE 2

| Entry | Catalyst Amt (mg) | Support | Supplier | Acetamido-sorbitol Conversion (%) | Acetamidogulonic Acid Yield (%) |
|---|---|---|---|---|---|
| 1 | 9 | Titania P25 | Arcos Organics | 66 | 37 |

B. Preparation of Amidocaproic Acid from Amidogulonic Acid Product

Preparation of 1.06 wt. % Pd-1.03 wt. % Rh/Silica Catalyst:

10 g of dried Silica Davisil 635, pore size 60 Å, 60-100 mesh (Aldrich) was weighed into a vial. Suitably concentrated Pd—Rh stock solution was prepared from concentrated acidic stock solutions purchased from Heraeus. Multiple additions of the Pd—Rh stock solution were added to the silica (silica pore volume=0.88 mL/g) until a total volume of 8.8 mL was reached. After each addition, the mixtures were agitated to impregnate the silica. Post impregnation, the Pd—Rh/Silica mixtures were dried in a furnace at 60° C. for 12 hours, after which the sample was reduced at 200° C. under forming gas for 3 hours. Upon cooling the catalyst was stored in a desiccator until used.

Example 3

50 mg of 1.06 wt. % Pd-1.03 wt. % Rh/Silica catalyst was transferred to a 1 mL glass vial insert. The vial received a glass bead and 250 μL of a solution containing 12 mg of amidogulonic acid product (acetamidogulonic acid and the other reaction products from the experiment reported in Table 1, entry 12, product was dried under vacuum and used directly) and 0.4M HI (Spectrum Chemicals) in Acetic Acid (Sigma-Aldrich). The vial was then covered with a Teflon pin-hole sheet, a silicone pin-hole mat and a gas diffusion plate. The vial insert was placed in a pressure vessel, pressurized and vented 3 times with nitrogen and 3 times with hydrogen before being pressurized with hydrogen to 900 psig, heated to 160° C. and shaken for 90 minutes. The reactor was then cooled, vented and purged with nitrogen. An aliquot of the reaction sample was then diluted with water and analyzed by mass spectrometry. The yields of 6-aminocaproic acid and 6-acetamidocaproic acid were 5% and 13% respectively.

C. Preparation of Amino and Amidocaproic Acid Product

Example 4

20 mg of 1.06 wt. % Pd-1.03 wt. % Rh/Silica catalyst was transferred to 1 mL glass inert. The vial received a glass bead and 100 μL of a solution containing 0.2 M of 6-amino-6-deoxygluconic acid sodium salt (Acme Bioscience, Inc.) and 0.6 M HI (Spectrum Chemicals) in acetic acid (Sigma-Aldrich). The vial was then covered with a Teflon pin-hole sheet, a silicone pin-hole mat and a gas diffusion plate. The vial insert was placed in a pressure vessel, pressurized and vented 3 times with nitrogen and 3 times with hydrogen before being pressurized with hydrogen to 900 psig, heated to 160° C. and shaken for 90 min. The reactor was then cooled, vented and purged with nitrogen. An aliquot of the reaction sample was then diluted with water to generate a sample for analysis by mass spectrometry. The yield of 6-aminocaproic acid and 6-acetamidocaproic acid were 22% and 3% respectively.

We claim:

1. A process for preparing an amino or amidocaproic acid product, the process comprising:

reacting, in the presence of a hydrodeoxygenation catalyst comprising at least a first metal selected from the group consisting of palladium, iridium, and rhodium and a halogen source, an amino or amido polyhydroxy acid substrate and hydrogen to convert at least a portion of the amino or amido polyhydroxy acid substrate to the amino or amidocaproic acid product, wherein the amino or amido polyhydroxy acid substrate is a compound of formula IIa and the amino or amidocaproic acid product is a compound of formula III:

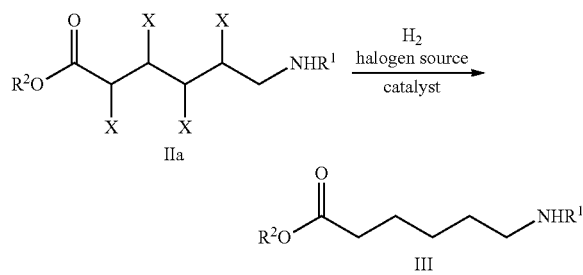

wherein each X is independently hydroxyl, oxo, halo, or acyloxy;

wherein $R^1$ is acyl, substituted acyl, aroyl, substituted aroyl, or hydrogen; and wherein $R^2$ is a salt-forming ion, hydrogen, or a lactone thereof.

2. The process of claim 1, wherein each X is hydroxyl.
3. The process of claim 1 or 2, wherein $R^1$ is acyl.
4. The process of claim 1 or 2, wherein $R^1$ is acetyl.
5. The process of claim 1 or 2, wherein the amino or amido polyhydroxy acid substrate is 6-amino-6-deoxygulonic acid or 6-N-acetamino-6-deoxygulonic acid.
6. The process of claim 1 or 2, wherein the amino or amido polyhydroxy acid substrate is 6-N-acetamido-6-deoxygulonic acid.
7. The process of claim 1 or 2, wherein the hydrodeoxygenation catalyst comprises a heterogeneous catalyst.
8. The process of claim 7, wherein the hydrodeoxygenation catalyst comprises a second metal selected from the group consisting of Ru, Rh, Pd, Pt, Ir, and Au, provided the second metal is different than the first metal.
9. The process of claim 8, wherein the hydrodeoxygenation catalyst comprises palladium and rhodium.
10. The process of claim 1 or 2, wherein the hydrodeoxygenation catalyst is a supported catalyst and the support is selected from the group consisting of silicas and zirconias.
11. The process of claim 1 or 2, wherein the halogen source is selected from the group consisting of ionic, atomic and molecular forms of iodine and bromine.
12. The process of claim 1 or 2, wherein the halogen source is hydrogen iodide or hydrogen bromide.
13. The process of claim 12, wherein the halogen source is hydrogen iodide.
14. The process of claim 1 or 2, wherein the molar ratio of halogen source to amino or amido polyhydroxy acid substrate is at least about 1.
15. The process of claim 1 or 2, wherein the reaction is maintained at a temperature of at least about 80° C.
16. The process of claim 1 or 2, wherein the reaction is maintained at a temperature of about 100° C. to about 200° C.
17. The process of claim 1 or 2, wherein the reaction is maintained at a temperature of about 120 to about 180° C.
18. The process of claim 1 or 2, wherein the reaction is conducted under a partial pressure of hydrogen in the range of from about 15 psia (104 kPa) to about 2000 psia (13790 kPa).
19. The process of claim 1 or 2, wherein the reaction is conducted under a partial pressure of hydrogen in the range of from about 300 psia (2069 kPa) to about 1500 psia (10342 kPa).
20. The process of claim 1 or 2, wherein at least a portion of the amino or amido polyhydroxy acid substrate is derived from glucose.
21. The process of claim 20, wherein at least a portion of the glucose is derived from a carbohydrate source.
22. The process of claim 1 or 2, wherein the reaction further comprises a weak carboxylic acid, and wherein at least a portion of the amino or amido polyhydroxy acid substrate is solubilized with the weak carboxylic acid.
23. The process of claim 22, wherein the pKa of the weak carboxylic acid is at least about 4.5.
24. The process of claim 22, wherein the weak carboxylic acid is acetic acid.
25. A process for preparing an amidocaproic acid compound from glucose, the process comprising:

converting glucose to a cyclic amido polyol compound of formula IV:

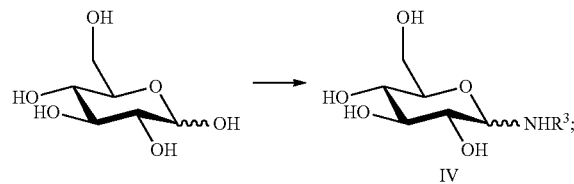

wherein $R^3$ is acyl, substituted acyl, aroyl, or substituted aroyl;

reacting, in the presence of an oxidation catalyst, at least a portion of the cyclic amido polyol compound and an oxidant to convert at least a portion of the cyclic amido polyol compound to a cyclic polyhydroxy acid compound of formula V:

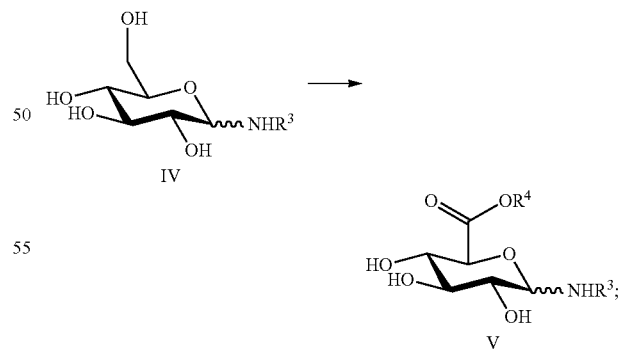

wherein $R^3$ is as defined above and $R^4$ is a salt-forming ion or hydrogen; and reacting, in the presence of a hydrodeoxygenation catalyst comprising at least a first metal selected from the group consisting of palladium, iridium, and rhodium and a halogen source, at least a portion of the cyclic polyhydroxy acid compound and hydrogen to convert at least a portion of the cyclic polyhydroxy acid compound to an amidocaproic acid compound of formula VI:

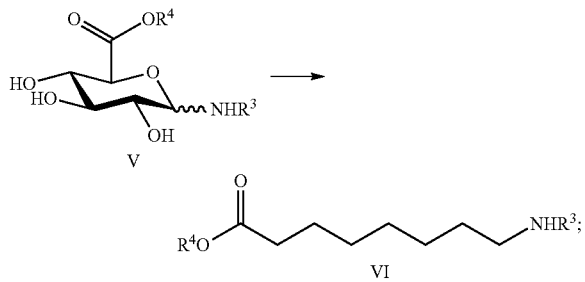

wherein $R^3$ and $R^4$ are as defined above.

26. A process for preparing an amidocaproic acid product, the process comprising:

converting an amidopolyol substrate to an amido polyhydroxy acid substrate, wherein the amidopolyol substrate is a compound of formula I:

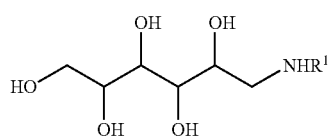

wherein $R^1$ is acyl, substituted acyl, aroyl or substituted aroyl; and wherein the amido polyhydroxy acid substrate is a compound of formula IIa:

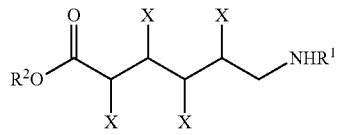

wherein X is hydroxyl, wherein $R^1$ is as defined above, and wherein $R^2$ is a salt-forming ion, hydrogen, or a lactone thereof; and reacting, in the presence of a hydrodeoxgenation catalyst comprising at least a first metal selected from the group consisting of palladium, iridium, and rhodium and a halogen source, the amido polyhydroxy acid substrate and hydrogen to convert at least a portion of the amido polyhydroxy acid substrate to an amidocaproic acid product, wherein the amidocaproic acid product is a compound of formula III:

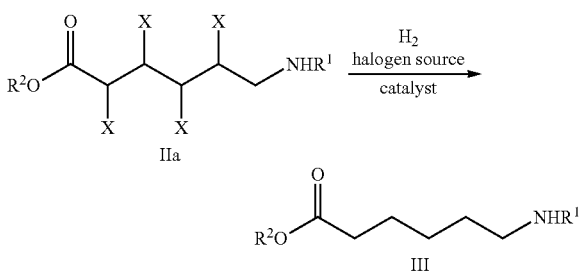

wherein X, $R^1$, and $R^2$ are as defined above.

27. The process of claim 26, wherein the amidopolyol substrate is converted to the amido polyhydroxy acid substrate by reacting the amidopolyol substrate with oxygen in the presence of an oxidation catalyst.

28. The process of claim 27, wherein the oxidation catalyst comprises a heterogeneous catalyst.

29. The process of claim 28, wherein the oxidation catalyst comprises a metal selected from the group consisting of palladium and platinum.

30. The process of claim 26, wherein the amidopolyol substrate is 6-amido-6-deoxysorbitol or 6-N-acetamido-6-deoxysorbitol.

* * * * *